(12) United States Patent
Jonsson

(10) Patent No.: US 11,382,783 B2
(45) Date of Patent: Jul. 12, 2022

(54) ORTHOSIS, USE OF SUCH ORTHOSIS AND KIT OF PARTS

(71) Applicant: Camp Scandinavia AB, Helsingborg (SE)

(72) Inventor: Maria Jonsson, Helsingborg (SE)

(73) Assignee: CAMP SCANDINAVIA AB, Helsingborg (SE)

( * ) Notice: Subject to any disclaimer, the term of this patent is extended or adjusted under 35 U.S.C. 154(b) by 244 days.

(21) Appl. No.: 16/458,317

(22) Filed: Jul. 1, 2019

(65) Prior Publication Data

US 2020/0015991 A1 Jan. 16, 2020

(30) Foreign Application Priority Data

Jul. 16, 2018 (SE) .................................... 1850905-9

(51) Int. Cl.
*A61F 5/01* (2006.01)
*A61F 13/08* (2006.01)

(52) U.S. Cl.
CPC .......... *A61F 5/0109* (2013.01); *A61F 5/0111* (2013.01); *A61F 5/0118* (2013.01)

(58) Field of Classification Search
CPC ........ A61F 5/0106–0111; A61F 5/0118; A61F 5/0123–013; A61F 5/01–0111;
(Continued)

(56) References Cited

U.S. PATENT DOCUMENTS 1,995,261 A * 3/1935 Gidney .................. A41B 11/12
2/338
3,727,812 A * 4/1973 Weiss .................... A47G 25/905
223/111
(Continued)

FOREIGN PATENT DOCUMENTS

DE 4106994 9/1991
DE 202009012967 12/2009
EP 2407128 1/2012

OTHER PUBLICATIONS

Search Report and Office Action SE Application 1850905-9 dated Jan. 31, 2019.
(Continued)

*Primary Examiner* — Michelle J Lee
(74) *Attorney, Agent, or Firm* — Grasso PLLC

(57) ABSTRACT

The disclosure relates to an orthosis comprising a tubular sleeve having an inlet opening and an outlet opening or sock. The tubular sleeve is preferably formed of a stretchable, textile-based material such that the tubular sleeve as such is radially collapsible when being in a non-worn condition and is circumferentially stretchable to adapt to a shape of a limb of a user when being worn thereon. The orthosis further comprises a circumferentially expandable reinforcement member arranged at the inlet opening and circumscribing at least approximately 135° of the inlet opening. The reinforcement member is resilient and provides a radially outwardly directed force onto the tubular sleeve and thereby retains the inlet opening in an open shape facilitating insertion of the limb through the inlet opening into the orthosis. Also described are kit of parts and the use of the orthosis.

19 Claims, 6 Drawing Sheets

(58) Field of Classification Search
CPC . A61F 13/06–108; A47G 25/80; A47G 25/86; A47G 25/90; A47G 25/905–908; A47G 25/92; A47G 25/84; A47G 25/904–908; A41B 11/02; A41B 11/04; A41B 11/12; A41B 11/123; A41B 11/125
See application file for complete search history.

(56) References Cited

U.S. PATENT DOCUMENTS

| | | | | |
|---|---|---|---|---|
| 5,154,690 | A * | 10/1992 | Shiono | A61F 5/0102 602/61 |
| 7,025,738 | B2 * | 4/2006 | Hall | A61F 5/0109 128/882 |
| 7,076,973 | B1 * | 7/2006 | Chesebro, Jr. | A41B 11/00 2/239 |
| 7,975,886 | B2 * | 7/2011 | McAllister | A47G 25/905 223/111 |
| 8,894,594 | B2 * | 11/2014 | Pflaster | A61B 5/1071 602/16 |
| 2002/0139819 | A1 * | 10/2002 | Ferraioli | A47G 25/908 223/111 |
| 2005/0240283 | A1 | 10/2005 | Kania | |
| 2012/0228343 | A1 | 9/2012 | Brobeg | |
| 2013/0053743 | A1 | 2/2013 | Reinhardt et al. | |
| 2014/0151412 | A1 * | 6/2014 | Cohen | A47G 25/905 223/111 |
| 2014/0263486 | A1 * | 9/2014 | Taylor | A47G 25/908 223/111 |
| 2018/0042754 | A1 | 2/2018 | Ingimundarson et al. | |

OTHER PUBLICATIONS

EP19182355 Extended European Search Report and EPO Communication, dated Dec. 12, 2019 (8pp).

* cited by examiner

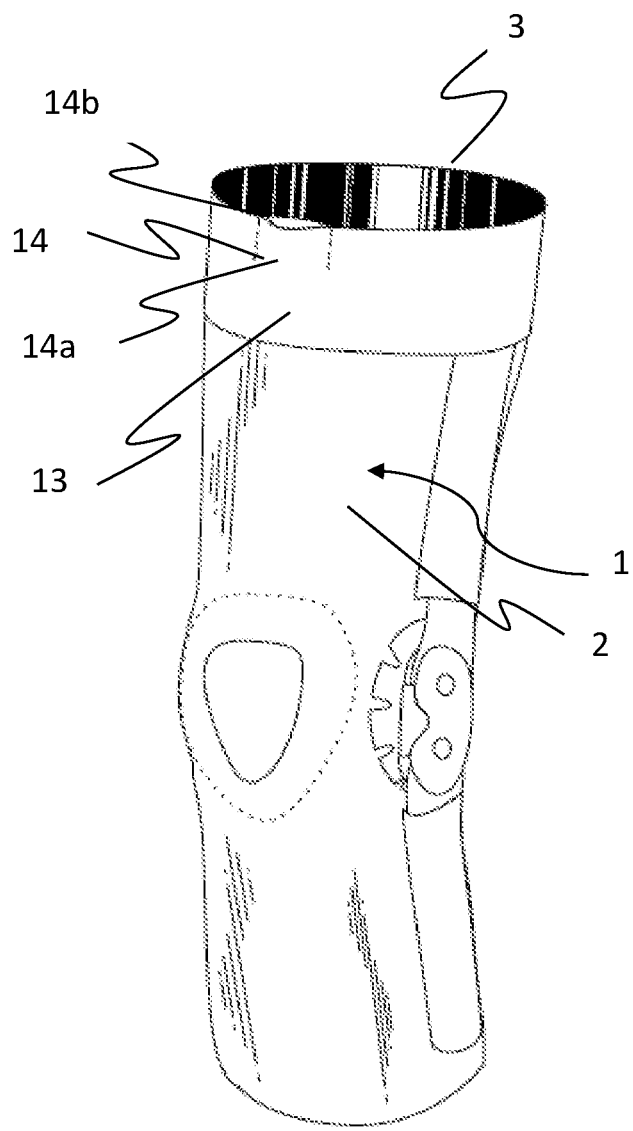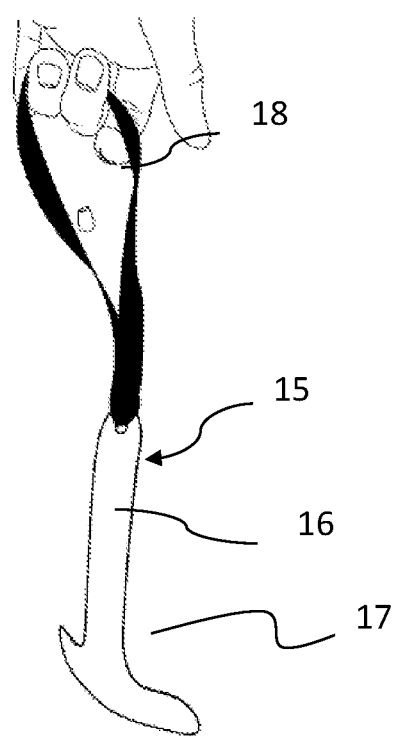
Fig. 3A                    Fig. 3B

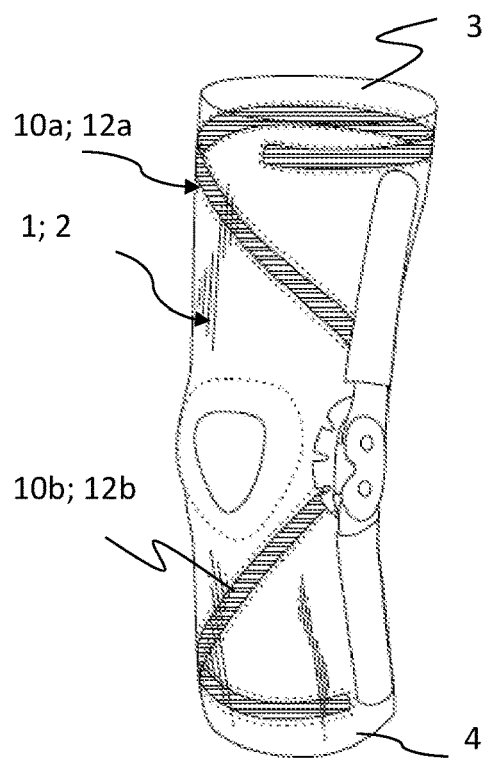
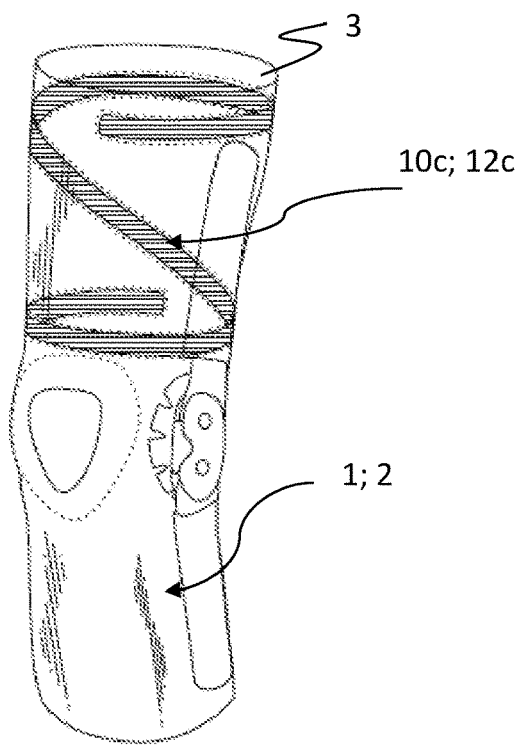
Fig. 5    Fig. 6
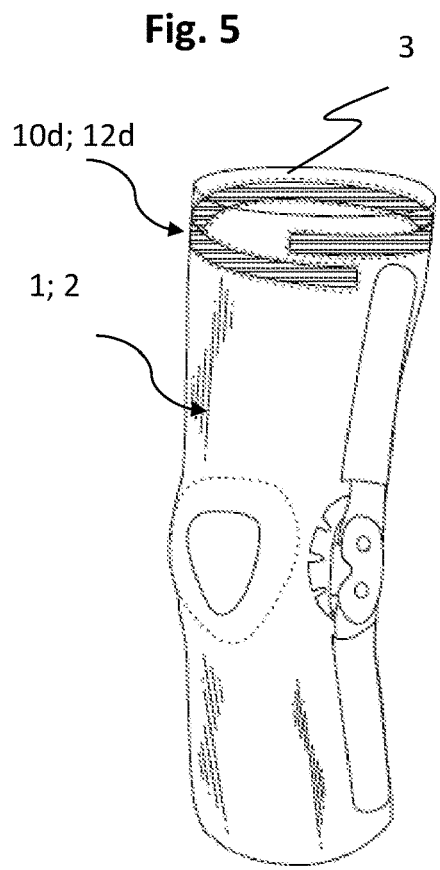
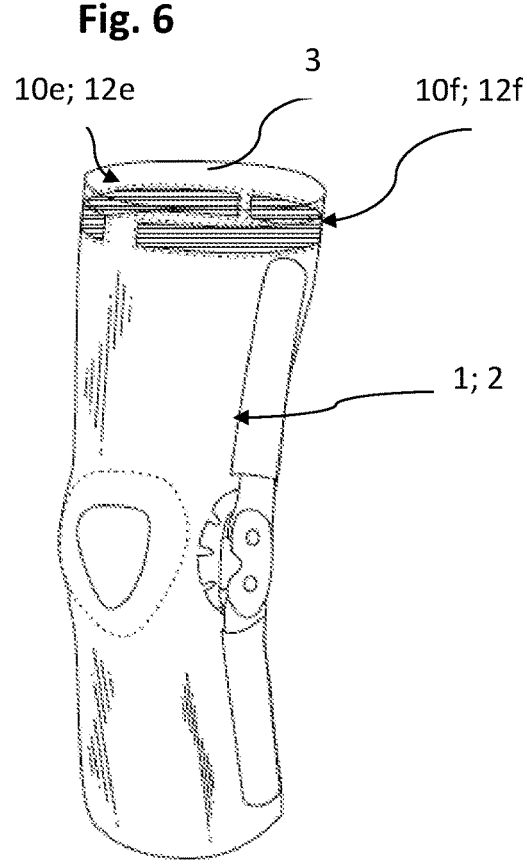
Fig. 7    Fig. 8

ORTHOSIS, USE OF SUCH ORTHOSIS AND KIT OF PARTS

CROSS-REFERENCE TO RELATED APPLICATION

This application claims priority to Swedish patent application number 1850905-9, which was filed on Jul. 16, 2018, and is entitled An Orthosis, Use of Such Orthosis and Kit of Parts. The '905-9 application is incorporated by reference, in its entirety, into this application.

TECHNICAL FIELD

The invention relates to an orthosis, the use of such orthosis, and also a kit of parts, where said kit comprises the orthosis and a pulling tool.

BACKGROUND

Orthoses are often considered to be devices, external of the body, that serve to or are used to alter, modify, or support, structural and/or functional characteristics of the body's skeletal or neuromuscular systems. For example, an orthosis may be used to assist a person having a reduced proprioception, i.e. a reduced ability to sense stimuli arising within the body regarding position, motion, and equilibrium. Orthoses can provide confinement and support in static situations, such as in retarding further spinal curving of a patient with scoliosis, and in dynamic situations, such as with supporting and influencing gait of a patient suffering from drop foot. An orthosis may also immobilize, limit, steer, guide, or dictate the position or range of movement of a body extremity, a body joint, or a body area. Accordingly, orthoses may be used for e.g. treatment, improved lifestyle, and improved comfort no matter if the orthosis is used temporarily by an otherwise fit person or by a person having a lifelong impairment.

In cases where the orthosis is intended to be used for a body extremity, such as an arm, a knee or a foot, the orthosis is typically either of a wrap type or a tubular type. An orthosis of the wrap type has a substantially flat or single-curved extension when not in use and is wrapped around the limb and attached thereto by using one or more straps. This kind of orthosis is difficult to use not only for persons having a reduced proprioception or a reduced physical ability, but also for otherwise fit persons since it requires two or more well-functioning hands to hold the orthosis during wrapping and tensioning the straps.

An orthosis of the tubular type comprises a tubular sleeve having an inlet opening and an outlet opening. To be used, the limb is inserted into the inlet opening and then the tubular sleeve is pulled along the limb to the correct position, such as over a knee. An orthosis of the tubular type is typically formed of a stretchable, textile-based material, whereby the tubular sleeve as such has a radially collapsible cross section when not in use. Further, it is circumferentially stretchable to adapt to the shape of a limb when put on. The radially collapsible cross section of the inlet opening results in that it may be experienced as being difficult to sight, reach and operate the inlet opening with the hand or the foot for a person having a reduced hand function, poor balance or otherwise reduced physical ability. Further, not only should the inlet opening be sighted, but then the tubular sleeve must be grasped and pulled along the limb, which requires an ability to firmly grasp and pull the tubular sleeve. Since the orthosis in many cases should have a rather snug fit, it may require a substantial effort and that the rest of the body should be bent to facilitate the operation.

BRIEF DESCRIPTION OF THE DRAWINGS

The appended figures are provided to illustrate the general structures of embodiments. Like reference numerals refer to like elements throughout.

FIG. 3A illustrates a perspective view of the orthosis of FIG. 1 as may be positioned for use with a pulling tool as may be employed in embodiments.

FIG. 3B illustrates a pulling tool as may be employed in embodiments.

FIG. 5 illustrates a perspective view of the orthosis of FIG. 1 with multiple reinforcing members as may be employed in embodiments.

FIG. 6 illustrates a perspective view of the orthosis of FIG. 1 with a reinforcing member as may be employed in embodiments.

FIG. 7 illustrates a perspective view of the orthosis of FIG. 1 with a reinforcing member as may be employed in embodiments.

FIG. 8 illustrates a perspective view of the orthosis of FIG. 1 with multiple reinforcing members as may be employed in embodiments.

DETAILED DESCRIPTION

Figures 1, 2:
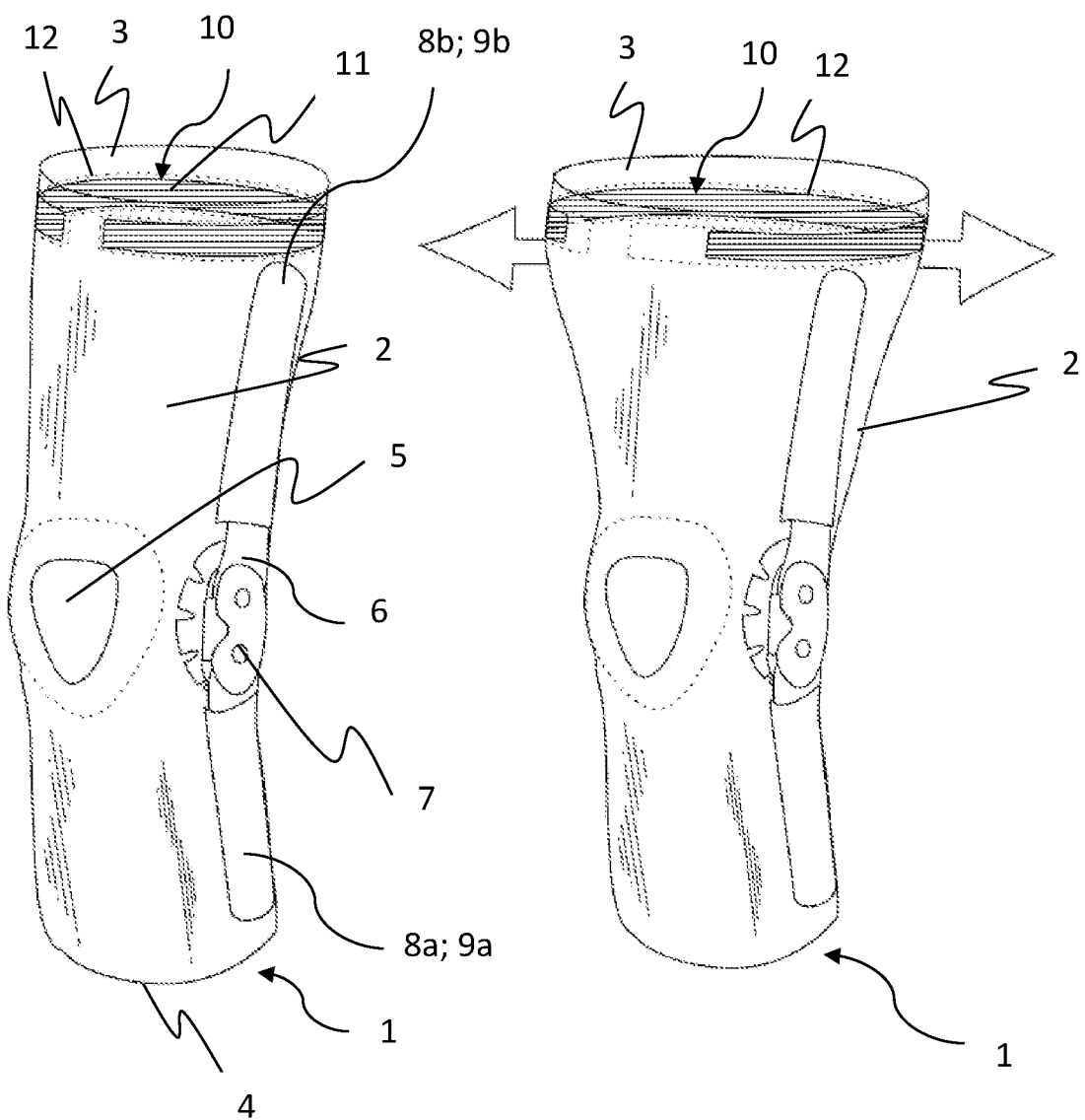
FIG. 1 illustrates a perspective view of an orthosis as may be employed in embodiments.
FIG. 2 illustrates a perspective view of the orthosis of FIG. 1 with its inlet opening in a stretched position as may be employed in embodiments.

Embodiments may provide processes, devices, and systems directed to the placement or adjustment or use of an orthosis. This may include placement of an orthosis by a person suffering from reduced proprioception, reduced motoric ability or a reduced hand force. Accordingly, embodiments may provide systems, devices, and processes directed to placement of an orthosis with reduced force or in a simplified manner to make the orthosis easy to use and put on to the body limb no matter the type of physical ability of a wearer. Embodiments, may, therefore, include an orthosis that is easily used by persons suffering from a reduced proprioception or a reduced physical ability such as reduced hand function, poor balance, or a reduced motoric ability. Embodiments may also be comfortable when worn.

Embodiments may comprise an orthosis comprising a tubular sleeve having an inlet opening, where the tubular sleeve may be formed of a stretchable, textile based material such that the tubular sleeve as such may be radially collapsible when being in a non-worn condition and may be circumferentially stretchable to adapt to a shape of a limb of a user when being worn thereon. In embodiments, the orthosis may further comprise a circumferentially expandable reinforcement member arranged at the inlet opening and circumscribing at least approximately 135° of the inlet opening, and wherein the reinforcement member may be resilient and may provide a radially outwardly directed force onto the tubular sleeve and thereby retain the inlet opening in an open shape facilitating insertion of the limb through the inlet opening into the orthosis.

In embodiments, an orthosis may be provided that, when not in use, has an inlet opening that may be readily accessible and may be easy to sight for insertion of a limb for persons having a reduced hand function, poor balance or a reduced motoric ability. Thus, in embodiments, the reinforcement member may be configured to provide a radially outwardly directed force onto the area in and around the inlet opening of the tubular sleeve. The reinforcement member may, thereby, expand the inlet opening into an open shape which may be easily accessible and may be easy to sight for insertion of the limb such as for persons having a reduced hand function, poor balance, or a reduced motoric ability. Accessibility may be advantageous in the case of a foot or knee orthosis of embodiments, which may require bending of the body to access and sight the inlet opening by a patient. Further, since the reinforcement member may be resilient in embodiments, it may adapt to the shape of the limb when worn. The resiliency may preferably contribute to overall comfort when wearing the orthosis.

The expandable reinforcement member may be selected from a group consisting of a spiral having at least approximately one full turn, a wire forming an open loop, and a slit tube. Other reinforcement member materials may also be employed. The expandable reinforcement member may preferably, no matter if it is provided by a spiral, a wire or a slit tube, form a gap which allows the expandable reinforcement member to gradually adapt to the circumference of the limb as the tubular sleeve is pulled along the limb. Still, the expandable reinforcement member may preferably have an inherent rigidity that retains the inlet opening in an open shape when the orthosis is not in use. In the case of a slit tube, the slit is preferably arranged to have an extension along the longitudinal extension of the tubular sleeve or forming an angle thereto. It is to be understood that two or more reinforcement members may be arranged one after the other, as seen along the longitudinal extension of the tubular sleeve. It is also to be understood that in embodiments the reinforcement member preferably may not only be arranged adjacent the inlet opening, but may also extend away from the inlet opening.

The reinforcement member may comprise a plastic material, a composite material, a metal, and combinations thereof. The resiliency and the ability to provide the radially outwardly directed force onto the inlet opening of the tubular sleeve may be arranged for by providing the expandable reinforcement member with a diameter that is larger than the normal, i.e. un-tensioned diameter of the inlet opening, whereby the material of the tubular sleeve can provide a biasing of the reinforcement member towards a smaller diameter.

In embodiments, the reinforcement member may be movably received in a channel extending along the circumference of the inlet opening. Thereby, no matter if the reinforcement member is forced to expanding or retracting, the reinforcement member can be allowed to freely move inside the channel. Also, in embodiments, the expandable reinforcement member may circumscribe at least approximately 180° and less than approximately 900° of the inlet opening and more preferred at least approximately 270° and less than approximately 720° of the inlet opening.

In embodiments, the tubular sleeve may comprise a through-going channel, a fold or a loop configured to present an engagement portion. In embodiments, an engagement portion may be configured to interact with a user's fingers, a pulling tool, or the user's or an assistant's fingers facilitating pulling the orthosis over the limb. In embodiments, the engagement portion may be arranged in an area adjacent the expandable reinforcement member, whereby the engagement portion may provide direct or indirect access to the reinforcement member. Thus, in embodiments, the pulling tool may engage the reinforcement member directly or indirectly as the orthosis is pulled along the limb.

In embodiments, a pulling tool may be provided as a longitudinal handle having a hook or a projection in one of its free ends. The hook or projection may be configured to engage the engagement portion of the tubular sleeve to thereby provide a firm grip of the orthosis during pulling. In embodiments, it may be preferred that the hook or the projection has an extension in the circumferential direction of the tubular sleeve. Thereby a larger contact surface between the orthosis and the pulling tool may be provided for, which may reduce the risk of tearing the material in the orthosis, when pulling the orthosis along the limb.

In embodiments, where the engagement portion in the tubular sleeve is a through-going channel, the longitudinal handle may be configured to be inserted into the channel and pulled in view of the tubular sleeve towards a position where the hook or projection directly or indirectly engages the reinforcement member. As the pulling continues, the reinforcement member may act as an enlarged contact surface, which can reduce the risk of tearing the material in the orthosis when pulling the orthosis along the limb.

In embodiments where the handle of the pulling tool has a longitudinal extension, the user may not have to bend his/her body to the same extent to reach and handle the orthosis. Also, any reduced motoric ability in the hand or fingers influencing the ability to grip a thin-walled orthosis may be overcome here, and in other embodiments, as a user may grip the handle of the pulling tool by a hammer grip rather than by the fingers only.

In the embodiment, where the engagement portion in the tubular sleeve is a loop, the loop may be preferably arranged either on the front side of the orthosis where it is easily visible or along two opposing longitudinal side portions of the tubular sleeve, thereby allowing pulling by two hands.

In embodiments, the tubular sleeve may further comprise a second opening. Thereby, the tubular sleeve may form a through-going channel which can be pulled along a limb. In the event the tubular sleeve only comprises an inlet opening, the other end of the tubular sleeve may be a closed end provided with a sock member attached to or integrated with the tubular sleeve. Depending on the design of the sock member, the sock may provide a closed end or partially open end of the tubular sleeve.

In embodiments, a tubular sleeve may further comprise a supporting rail having an extension along the longitudinal extension of the tubular sleeve. The supporting rail may be a hinged joint that assists and/or controls bending of the body joint. When orthoses support a knee, it may be preferred that two supporting rails be employed, one on each side of the tubular sleeve. The supporting rail may be preferably removably mounted to the orthosis to facilitate washing and the supporting rail may be received in a pocket arranged in the tubular sleeve.

Embodiments may include knee orthoses, ankle-foot orthoses, leg orthoses, hand orthoses, arm orthoses, and elbow orthoses. Other orthoses may also be employed in embodiments.

The tubular sleeve may be made of a woven or knitted elastic material such as elastomer or a combination of elastomer and polyester. The tubular sleeve may comprise padding portions of a foamed plastics material, a synthetic-rubber material such as chloroprene rubber, a 3D spacer fabric, or a fiberfill foam. The density of the padding portions may be approximately 1-70 shore and more preferred approximately 5-60 shore. It is to be understood that a combination of different types of materials and properties may be used in embodiments. Also, it is to be understood that the tubular sleeve may be provided by two or more panels being joined, or by circular knitting in embodiments.

Other aspects of embodiment may include a kit of parts comprising an orthosis as taught and a pulling tool. A further scope of applicability of embodiments may become apparent from the description of the figures. However, the detailed description, figures, and examples, while indicating preferred embodiments, are given by way of illustration only, since various changes and modifications within the scope of the disclosure are also possible. Hence, it is to be understood that embodiments are not limited to the particular component parts of the devices and systems and processes described. It is also to be understood that the terminology used herein is for the purpose of describing embodiments, and is not intended to be limiting.

It is further noted that, as used in the specification and the appended claims, the articles "a," "an," "the," and "said" are intended to mean that there are one or more of the elements unless the context clearly dictates otherwise. Thus, for example, reference to "a unit" or "the unit" may include several devices, and the like. Furthermore, the words "comprising", "including", "containing" and similar wordings does not exclude other elements or steps.

FIG. 1 shows a schematic perspective view of a knee orthosis as may be employed in embodiments. The principles, design features, and other aspects described with respect to the knee orthosis of FIG. 1 and other Figures may also be employed in other types of orthoses, which may include ankle-foot orthoses, leg orthoses, hand orthoses, arm orthoses, and elbow orthoses, as well as other types.

The orthosis 1, of FIG. 1, comprises a tubular sleeve 2 having a longitudinal orientation along with an inlet opening 3 and an outlet opening 4. In the context of the description, the "inlet opening" refers to the opening into which the limb is intended to be inserted when putting on the orthosis. The inlet opening 3 and the outlet opening 4 may be provided with different diameters to account for the anatomy of the human body. The tubular sleeve 2 should preferably adapt to the shape of a limb, which as such has no mathematical diameter. Hence, the term "diameter" should in the context of the invention be understood as relating to the width of a portion of a limb. Also, to better adapt to the anatomy, the tubular sleeve 2 may have a frusto-conical shape with the diameter of the inlet opening 3 being larger than the diameter of the outlet opening 4.

The tubular sleeve 2 is preferably formed of a stretchable, textile-based material. The textile-based material may be a woven or knitted elastic material, such as elastomer or a combination of elastomer and polyester. The elastic material may also be made of natural materials such as cotton. The density of the elastic material may differ across the tubular sleeve. Thereby different properties may be provided for, such as improved breathing or locally reduced or increased support. The tubular sleeve 2 may be formed into its tubular shape by circular knitting or by joining one or several panels of material together. The joining method preferably depends on the type of material. Possible joining methods may, by way of example be, sewing, adhesive bonding or welding, depending on the type of material. Combinations of different joining methods may also be used. Also, the joints may be designed to contribute to the overall shape of tubular sleeve 2 and also to allow the tubular sleeve 2 to better accommodate to the anatomy.

The tubular sleeve 2 may be provided with one or more non-shown paddings. The padding material may be provided by a woven or knitted textile material, a foamed plastics material, a synthetic rubber material such as chloroprene rubber, a 3D spacer fabric, a fiberfill foam, or other material. A 3D spacer fabric is a three-dimensional knitted spacer fabric. In preferred embodiments the material selected should be flexible. The padding may be provided as a continuous homogenous surface or be provided with perforations or local cut-outs to adapt to the anatomy and any supporting rails. Further, the padding may be provided with different thickness across its surface area. In case of the tubular sleeve 2 being made by circular knitting, local areas may be provided with increased density or areas with another material to thereby form a padding.

No matter how the tubular sleeve 2 is formed, the material of the tubular sleeve 2 preferably has an inherent flexibility whereby the tubular sleeve 2 alone is radially collapsible when being in a non-worn condition and is circumferentially stretchable to adapt to a shape of a limb of a user when being worn thereon.

In FIG. 1, the orthosis 1 comprises an optional through-going opening 5 extending across the patella. Also, the disclosed orthosis 1 comprises an optional supporting rail 6 having an extension along the longitudinal extension of the tubular sleeve 2. Although only one supporting rail 6 is disclosed, it is to be understood that a corresponding second supporting rail may be arranged along the opposite longitudinal side of the tubular sleeve 2. The disclosed supporting rail 6 is provided with a hinged joint 7 configured to assist in and/or to control bending of the knee. The supporting rail 6 is disclosed as being removably mounted to the tubular sleeve 2 by its free opposing ends 8a, 8b being received in pockets 9a, 9b. Thereby the supporting rail 6 may be easily removed to facilitate washing.

The orthosis 1 comprises a circumferentially expandable reinforcement member 10. The reinforcement member 10 is arranged in an area adjacent the inlet opening 3 of the tubular sleeve 2. The reinforcement member 10, which in FIG. 1 is illustrated as a slit tube 11, is movably contained in a channel 12 that extends along the circumference of the inlet opening 3. It is to be understood that in the event the reinforcement member 10 is a slit tube 11 or a wire forming an open loop, the channel 12 may have two closed ends forming stops. If the reinforcement member 10 is a spiral having at least one full turn, the channel 12 should preferably have a continuous circumferential extension.

The reinforcement member 10, in preferred embodiments, may circumscribe at least approximately 135° of the inlet opening 3, preferably at least approximately 180° and less than approximately 900° of the inlet opening 3 and more preferred at least approximately 300° and less than approximately 720° of the inlet opening 3.

The reinforcement member 10 has in a condition before being contained in the channel 12, an unbiased form with a radius that corresponds to or slightly exceeds the un-stretched diameter of the inlet opening 3, which un-stretched diameter is provided by the tubular sleeve 2 in itself. Accordingly, when the reinforcement member 10 is contained in the channel 12, the reinforcement member 10 preferably will, due to its resiliency, strive to resume its unbiased form whereby it will provide a radially outwardly directed counter-force to the inner walls of the channel 12. Thereby the reinforcement member 10 will preferably retain the inlet opening 3 in an open shape when the orthosis 1 is not in use. The open shape facilitates sighting and insertion of the limb through the inlet opening 3 into the orthosis 1. It is to be understood that the open shape depends on the extension of the reinforcement member 10. By way of example, in the case where the reinforcement member 10 circumscribes approximately 180° of the inlet opening 3 a more or less half-circular inlet opening 3 will be provided, whereas a circumferential extension of more than approximately 270° will provide a substantially circular inlet opening 3. In embodiments, it is to be understood that the reinforcement member with remained function may be fixed to the tubular sleeve.

FIG. 2 illustrates the orthosis of FIG. 1 and schematically demonstrates the principle of the resilient reinforcement member. As can be seen in FIG. 2, in embodiments, as the tubular sleeve 2 is pulled along a limb (not shown) to cover a body portion having a larger diameter, such as a thigh, the material of the tubular sleeve 2 will stretch, see arrows, whereby the diameter of the inlet opening 3 will increase. This increase in diameter will allow the reinforcement member 10 to expand by moving inside the channel 12. The reinforcement member 10 will, hence, act as a spring that can accommodate to diameter changes that are larger, but also smaller than the unbiased diameter of the reinforcement member 10. Although FIG. 1 and FIG. 2 show the reinforcement member 10 as a slit tube 11, the reinforcement member 10 may with remained function be a wire forming a loop or a spiral having at least one full turn or other materials having expansion and contraction functionality compatible with the descriptions provided herein.

FIGS. 3A-3D schematically illustrate a process of arranging the orthosis along the limb of a user by using an embodiment of a pulling tool as may be employed in embodiments. FIGS. 3A-3D illustrate a kit of parts comprising an orthosis 1 and a pulling tool 15. The orthosis 1 has a design corresponding to that of FIGS. 1 and 2, i.e. with a reinforcement member (not shown), contained in a channel 12 (not shown), which extends in an area adjacent the inlet opening 3.

In FIG. 3A the orthosis 1 comprises an engagement portion 13 in the area of its inlet opening 3. The engagement portion 13 is formed as a through-going channel 14 extending transverse the longitudinal extension of the tubular sleeve 2. The through-going channel 14 has a downwardly directed inlet 14a and an upwardly directed outlet 14b.

In FIG. 3B an embodiment of the pulling tool 15 is disclosed. The pulling tool 15 comprises a longitudinally extending handle 16. The handle 16 has a T-shaped projection 17 in one of its free ends. The T-shaped projection 17 may have a slight single curved extension. The curvature may correspond to the curvature of the limb. The opposite free end of the handle 16 may be provided with an optional strap 18. The pulling tool 15 may be formed by e.g. injection molding a plastic material.

Figures 3C, 3D:
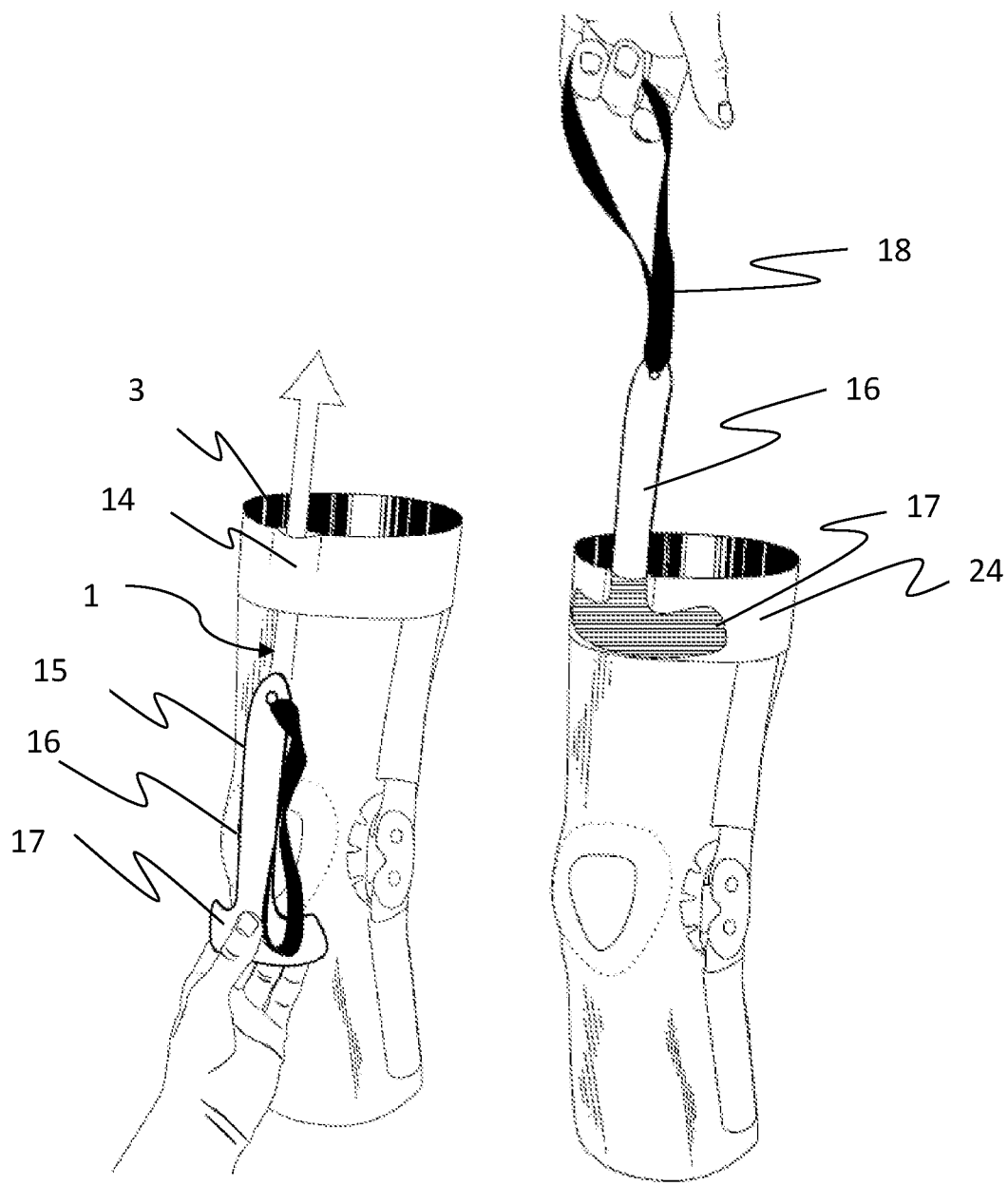
FIG. 3C illustrates a perspective view of the orthosis of FIG. 1 as may be positioned for use with a pulling tool as may be employed in embodiments.
FIG. 3D illustrates a perspective view of the orthosis of FIG. 1 as may be positioned for use with a pulling tool as may be employed in embodiments.

When using the pulling tool 15, see FIG. 3C and FIG. 3D, the free end of the handle 16 may be inserted into the inlet of the through-going channel 14 and pushed or pulled into a position where the T-shaped projection 17 abuts the lower edge of the reinforcement member (not shown) or is received in a fold 24. Thus, the pulling tool 15 may be arranged in direct or indirect contact with the reinforcement member.

In this position, the user may lift and move the orthosis 1 into a suitable position and then sight and insert the foot into the inlet opening 3 which as such is expanded by the reinforcement member, which may be located below the fold 24. The insertion is preferably made while the user at the same time holds the pulling tool 15 either by directly grasping the handle 16 or by holding the pulling tool 15 in its strap 18. As the foot has been correctly inserted, the orthosis 1 may be pulled along the limb into the correct position by pulling the handle 16. By the handle 16 of the pulling tool 15 having a longitudinal extension, the user does not have to unduly bend his/her body to reach and handle the orthosis. Also, any reduced motoric ability in the hand or fingers influencing the ability to grip a thin-walled orthosis 1 may be overcome since the user may grip the handle 16 by a hammer grip rather than by the fingers only. When the orthosis 1 has been correctly positioned to the limb, the pulling tool 15 may easily be removed by pulling the pulling tool 15 in the opposite direction.

The very same principle as described in Figures. 3A-3D is applicable if the pulling tool comprises two handles which are interconnected by a bridging projection. In such embodiment, not shown, the orthosis may be provided with two through-going channels 14, each configured to receive a handle.

Figures 4A, 4B:
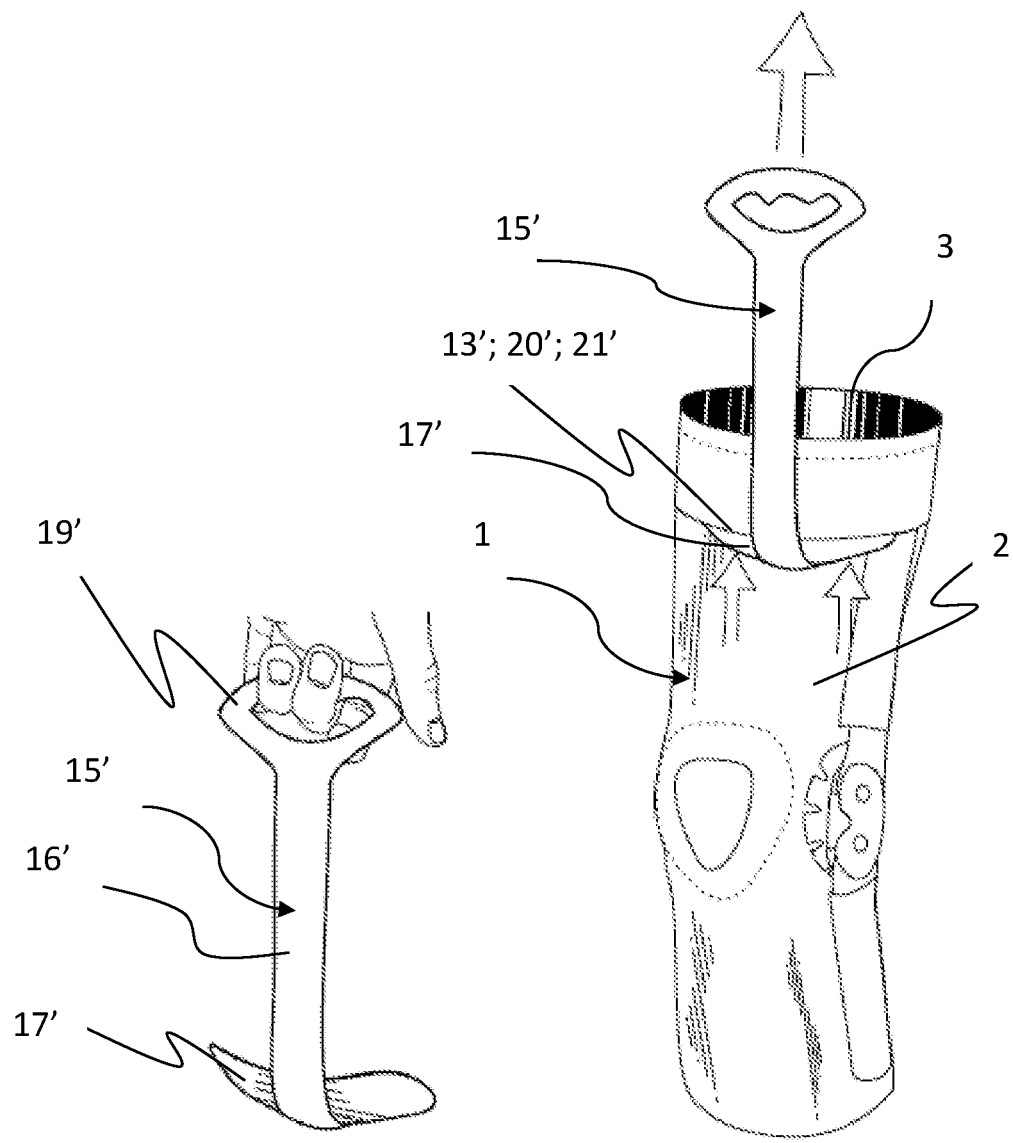
FIG. 4A illustrates a pulling tool as may be employed in embodiments.
FIG. 4B illustrates a perspective view of the orthosis of FIG. 1 as may be positioned for use with a pulling tool as may be employed in embodiments.

FIGS. 4A and 4B disclose schematically the principle of arranging the orthosis along the limb of a user by using a second embodiment of the pulling tool. FIGS. 4A-4B show an embodiment of a kit of parts comprising an orthosis 1 and a second embodiment of a pulling tool 15' and its operation.

As seen in FIG. 4A, the pulling tool 15' comprises a longitudinally extending handle 16' having a hook-shaped projection 17' in one of its free ends. The opposite free end of the handle 16' is provided with a grip 19'. It is to be understood that the grip 19', with remained function may be omitted or be replaced by a strap. The pulling tool 15' may be formed by e.g. injection molding a plastic material.

The pulling tool 15' together with one embodiment of the orthosis 1 is illustrated in FIG. 4B. The orthosis 1 comprises an engagement portion 13' in the area of its inlet opening 3. The engagement portion 13' is formed as a fold 20' having a downwardly directed opening 21' extending transverse the longitudinal extension of the tubular sleeve 2.

When using the pulling tool 15', the hook-shaped projection 17' is inserted to engage the opening 21' in the engagement portion 13'. In this position, the user may lift and move (see arrows) the orthosis 1 into a suitable position and then sight and insert the foot into the inlet opening 3 which as such is expanded by the reinforcement member (not shown) in the very same way as previously discussed in view of FIGS. 3C and 3D. When the orthosis 1 has been correctly positioned to the limb, the pulling tool 15' may easily be removed by pulling the pulling tool 15' in the opposite direction.

Figure 9:
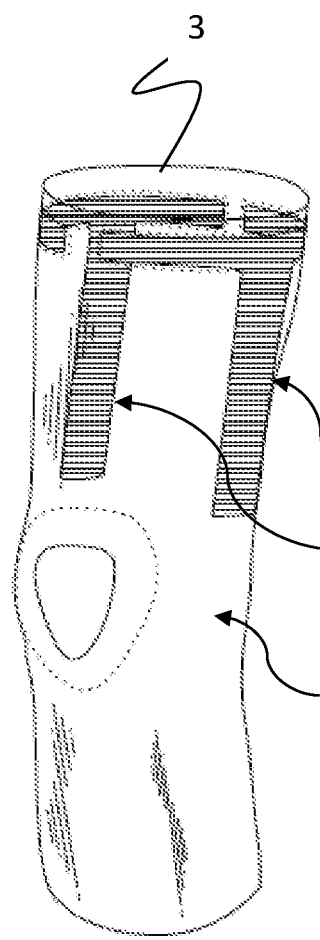
FIG. 9 illustrates a perspective view of the orthosis of FIG. 1 with multiple reinforcing members as may be employed in embodiments.

Among other things, FIGS. 5-10 disclose schematically different extensions of the reinforcement member. As disclosed in FIGS. 5-10 a number of embodiments of the reinforcement member 10 may be employed. The overall design of the orthosis 1 is the same as previously discussed and to avoid undue repetition, reference is made to previous sections. FIGS. 5-7 show examples of a reinforcement member 10 consisting of a spiral having at least one full turn while FIGS. 8-9 show reinforcing members formed from discontinuous non-spiral components.

In FIG. 5, a second embodiment of the reinforcement member is schematically disclosed. A first reinforcement member 10a is contained in a spiral-shaped channel 12a which extends along almost a full turn around the inlet opening 3 of the tubular sleeve 2 of orthosis 1 and then diagonally across the area of the tubular sleeve 2 above the patella. Further, a second reinforcement member 10b is arranged in the lower end of the tubular sleeve 2, where the second reinforcement member 10b is contained in a spiral-shaped channel 12b which extends along almost a full turn around the outlet opening 4 of the tubular sleeve 2 and then diagonally across the area of the tubular sleeve 2 below the patella. Accordingly, each reinforcement member 10a, 10b circumscribes its respective opening 3, 4 more than 360°. It is to be understood that the first and second reinforcement members 10a, 10b may have different extensions.

In FIG. 6, a third embodiment of the reinforcement member 10 is disclosed. The reinforcement member 10c is contained in a spiral-shaped channel 12c which extends along almost a full turn around the inlet opening 3 of the tubular sleeve 2 of orthosis 1 and then diagonally across the area of the tubular sleeve 2 above the patella where it makes almost a full turn.

FIG. 7 discloses a fourth embodiment of the tubular sleeve 2 of orthosis 1 with a reinforcement member 10d where the reinforcement member 10d is contained in a spiral-shaped channel 12d which extends along the inlet opening 3 of the tubular sleeve.

FIG. 8 discloses a fifth embodiment of the reinforcement member. The reinforcement member is divided into two parts 10e, 10f, each part extending in a channel 12e, 12f which extends along a part of the inlet opening 3 of the tubular sleeve 2 of orthosis 1.

FIG. 9 discloses a sixth embodiment of the orthosis 1. The orthosis comprises two reinforcement members 10g, 10h, each extending in a channel 12g, 12h along a portion of the full circumference of the inlet opening 3. Also, in this embodiment, each reinforcement member forms a longitudinal reinforcement along the longitudinal extension of the tubular member 2. At least the circumferential portions of the reinforcement members 10g, 10h are received in the channels 12g, 12h.

Figure 10:
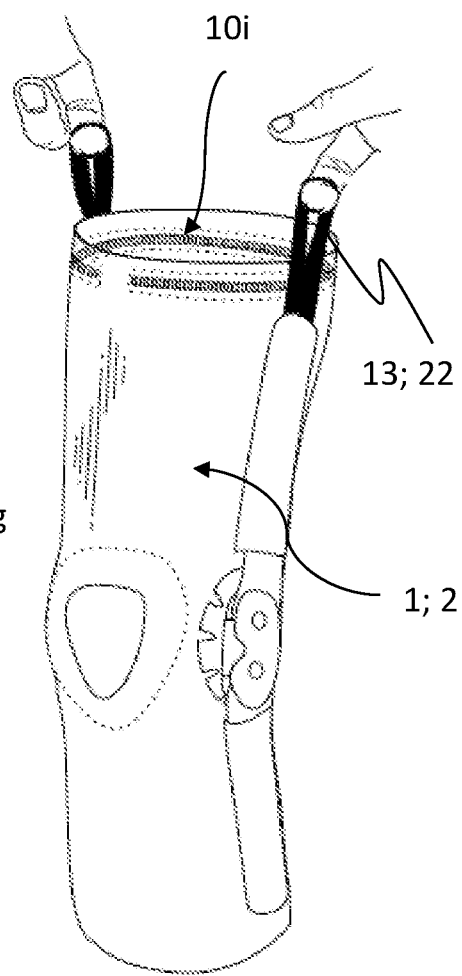
FIG. 10 illustrates a perspective view of the orthosis of FIG. 1 with a reinforcing member and multiple pull loops as may be employed in embodiments.

FIG. 10 discloses a seventh embodiment of the reinforcement member 10. The reinforcement member 10i is formed by a wire forming an open loop. This embodiment of the orthosis comprises an engagement portion 13 in the form of two loops 22 into which a user's or an assistant's fingers may be inserted to facilitate pulling the orthosis 1 over the limb. The two loops 22 are arranged along two opposing longitudinal side portions of the tubular sleeve 2. Other positions are equally possible.

As noted above, although the orthosis has been described as a knee orthosis, it is to be understood that embodiments may employ other types of orthoses, such as an ankle-foot orthosis, a leg orthosis, a hand orthosis, an arm orthosis, or an elbow orthosis.

Two types of pulling tools have been described. It is to be understood that the pulling tool and its dedicated engagement portion may be provided with different designs with remained function. The handle and its grip may be adapted to an individual person's physical needs or the type of orthosis. It is to be understood that an orthosis to be used on the foot or knee may require a pulling tool with a long handle to reduce the degree of bending the back to reach the floor/limb, whereas for a hand or elbow orthosis, it may be sufficient to only provide the orthosis with an engagement portion in the form of a loop configured to interact with a user's or an assistant's fingers.

The reinforcement member has been described as being loosely received in a channel adjacent the inlet opening. It is to be understood that the reinforcement member with remained function may be fixed to the tubular sleeve.

The tubular sleeve has been described and illustrated as a tubular sleeve having an inlet opening and an outlet opening. It is to be understood that the outlet opening may be omitted and replaced by a sock member which is attached to or integrated with the tubular sleeve.

Therefore, variations to the disclosed embodiments can be understood and effected by the skilled person in practicing the claimed invention, from a study of the drawings, the disclosure, and the appended claims. In other words, various features, steps, processes, components, and subcomponents, as may be employed in embodiments, are provided herein. These features, steps, processes, components, subcomponents, partial steps, systems, devices, etc. may be adjusted, combined and modified in various fashions and various ways among and between the teachings and figures provided herein, as well as in other ways not specifically described herein but consistent with the teachings and discussion of this disclosure.

The terminology used herein is for the purpose of describing particular embodiments only and is not intended to be limiting of the invention. As used herein, the singular forms "a," "an" and "the" are intended to include plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operation, elements, components, and/or groups thereof.

The corresponding structures, material, acts, and equivalents of any means or steps plus function elements in the claims below are intended to include any structure, material or act for performing the function in combination with other claimed elements that are specifically claimed.

Language such as "configured to" and "facilitate" connotes structure by indicating a device, such as a unit or a component, includes structure that performs a task or tasks during operation, and such, structure is configured to perform the task even when the device is not currently operational (e.g., is not on/active). A device "configured to" perform or "facilitate" one or more tasks is expressly intended to not invoke 35 U.S.C. § 112, (f) or sixth paragraph.

As used herein, the terms "about" or "approximately" in reference to a recited numeric value, including for example, whole numbers, fractions, and/or percentages, generally indicates that the recited numeric value encompasses a range of numerical values (e.g., +/−5% to 10% of the recited value) that one of ordinary skill in the art would consider equivalent to the recited value (e.g., performing substantially the same function, acting in substantially the same way, and/or having substantially the same result). As used herein, the terms "about" or "approximately" in reference to a recited characteristic, generally indicates that the recited characteristic encompasses a range of variations on the characteristic that one of ordinary skill in the art would consider equivalent to the recited characteristic (e.g., performing substantially the same function, acting in substantially the same way, and/or having substantially the same result).

The description of the present invention has been presented for purposes of illustration and description, but is not intended to be exhaustive or limited to the invention in the form disclosed. Many modifications and variations will be apparent to those of ordinary skill without departing from the scope and spirit of the invention. The embodiment was chosen and described in order to best explain the principles of the invention and the practical application, and to enable others of ordinary skill in the art to understand the invention for embodiments with various modifications as are suited to the particular use contemplated.

What is claimed is:

1. An orthosis system comprising:
a pulling tool; and
an orthosis, the orthosis comprising:
a tubular sleeve having an inlet opening, the tubular sleeve being formed of a stretchable, textile-based material such that the tubular sleeve is radially collapsible when being in a non-worn condition and is circumferentially stretchable to adapt to a shape of a limb of a user when being worn thereon,
wherein the tubular sleeve comprises a slit positioned at an uppermost edge of the tubular sleeve,
wherein the pulling tool is sized and configured to extend through the slit in the tubular sleeve,
wherein the orthosis further comprises a circumferentially expandable reinforcement member arranged at the inlet opening and circumscribing at least 135° of the inlet opening, and
wherein the reinforcement member is resilient and provides a radially outwardly directed force onto the tubular sleeve and thereby retains the inlet opening in an open shape to facilitate insertion of the limb through the inlet opening into the orthosis.

2. The orthosis system of claim 1, wherein the expandable reinforcement member is selected from the group consisting of a spiral having at least one full turn, a wire forming an open loop and a slit tube.

3. The orthosis system of claim 2, wherein the reinforcement member is movably received in a channel extending along a circumference of the inlet opening.

4. The orthosis system of claim 1 wherein the expandable reinforcement member circumscribes at least 180° and less than 900° of the inlet opening.

5. The orthosis system of claim 1 wherein the expandable reinforcement member circumscribes at least 270° and less than 720° of the inlet opening.

6. The orthosis system of claim 1 wherein the expandable reinforcement member is a spiral having at least one full turn.

7. The orthosis system of claim 1 wherein the tubular sleeve further comprises a supporting rail having an extension along a longitudinal extension of the tubular sleeve.

8. The orthosis system of claim 1 wherein the orthosis is a knee orthosis, an ankle-foot orthosis, a leg orthosis, a hand orthosis, an arm orthosis, or an elbow orthosis.

9. The orthosis system of claim 1 wherein the tubular sleeve is made of a woven or knitted elastic material comprising an elastomer or comprising a combination of elastomer and polyester.

10. An orthosis system comprising:
an elongated pulling tool; and
an orthosis, the orthosis comprising
a tubular sleeve having an inlet opening, the tubular sleeve being formed of a stretchable, textile-based material such that the tubular sleeve is radially collapsible when being in a non-worn condition and is circumferentially stretchable to adapt to a shape of a limb of a user when being worn thereon,
wherein the orthosis further comprises a circumferentially expandable reinforcement member arranged at the inlet opening and circumscribing at least 135° of the inlet opening,
wherein the tubular sleeve comprises a slit positioned at an uppermost edge of the tubular sleeve,
wherein the pulling tool is sized and configured to extend through the slit in the tubular sleeve, and
wherein the reinforcement member is resilient and provides a radially outwardly directed force onto the tubular sleeve and thereby retains the inlet opening in an open shape to facilitate insertion of the limb through the inlet opening into the orthosis.

11. The orthosis system of claim 10 wherein the pulling tool comprises a t-shaped distal end and a handle end.

12. The orthosis system of claim 11 wherein the t-shaped distal end is bent back and towards the handle end of the pulling tool and the distal-end is sized to fit within a folded portion of the orthosis.

13. The orthosis system of claim 10 wherein the slit includes a through-going channel, the through-going channel positioned at a fold of the tubular sleeve and further positioned along an upper rim crease of the fold of the tubular sleeve.

14. The orthosis system of claim 13 wherein the slit is sized to accept and let pass therewith a handle end of the pulling tool.

15. The orthosis system of claim 10 wherein the orthosis is a knee orthosis, an ankle-foot orthosis, a leg orthosis, a hand orthosis, an arm orthosis, or an elbow orthosis.

16. The orthosis system of claim 10 wherein the slit is positioned atop the uppermost edge of the tubular sleeve.

17. The orthosis system of claim 10 wherein the pulling tool comprises a t-shaped projection, a handle connected to the projection and a strap, the strap connected to the handle.

18. An orthosis system comprising:
a pulling tool;
a tubular sleeve having an inlet opening, the tubular sleeve being formed of a stretchable, textile-based material such that the tubular sleeve is radially collapsible when being in a non-worn condition and is circumferentially stretchable to adapt to a shape of a limb of a user when being worn thereon,
wherein the orthosis further comprises a first circumferentially expandable t-shaped reinforcement member arranged at the inlet opening and circumscribing at least 135° of the inlet opening,
wherein the reinforcement member has an elongated portion of its t-shape positioned along an elongated side of the tubular sleeve and has a top "t" portion of its t-shape positioned about the inlet opening of the tubular sleeve,
wherein the reinforcement member is resilient and provides a radially outwardly directed force onto the tubular sleeve and thereby retains the inlet opening in an open shape to facilitate insertion of the limb through the inlet opening into the orthosis,
wherein the tubular sleeve comprises a slit positioned at an uppermost edge of the tubular sleeve, and
wherein the Dulling tool is sized and configured to extend through the slit in the tubular sleeve.

19. The orthosis system of claim 18 further comprising a second expandable t-shaped reinforcement member arranged at the inlet opening of the tubular sleeve.

* * * * *